(12) United States Patent
Aflatoon

(10) Patent No.: US 8,343,194 B2
(45) Date of Patent: Jan. 1, 2013

(54) ANTERIOR CERVICAL STAPLE

(76) Inventor: Kamran Aflatoon, Corona del Mar, CA (US)

( * ) Notice: Subject to any disclaimer, the term of this patent is extended or adjusted under 35 U.S.C. 154(b) by 910 days.

(21) Appl. No.: 12/228,724

(22) Filed: Aug. 15, 2008

(65) Prior Publication Data
US 2009/0054930 A1 Feb. 26, 2009

Related U.S. Application Data

(60) Provisional application No. 60/965,471, filed on Aug. 20, 2007.

(51) Int. Cl.
A61B 17/80 (2006.01)
(52) U.S. Cl. ........................ 606/280; 606/290
(58) Field of Classification Search .................. 606/280, 606/75, 286, 297, 289, 290
See application file for complete search history.

(56) References Cited

U.S. PATENT DOCUMENTS

| | | | |
|---|---|---|---|
| 4,913,134 A | 4/1990 | Luque | |
| 5,084,049 A | 1/1992 | Asher et al. | |
| 5,129,899 A | 7/1992 | Small et al. | |
| 5,176,679 A | 1/1993 | Lin | |
| 5,261,910 A | 11/1993 | Warden et al. | |
| 5,352,229 A * | 10/1994 | Goble et al. | 606/75 |
| 5,364,399 A | 11/1994 | Lowery et al. | |
| 5,380,324 A | 1/1995 | Muller et al. | |
| 5,527,312 A | 6/1996 | Ray | |
| 5,549,612 A * | 8/1996 | Yapp et al. | 606/293 |
| 5,558,674 A | 9/1996 | Heggeness et al. | |
| 5,603,713 A | 2/1997 | Aust et al. | |
| 5,616,144 A | 4/1997 | Yapp et al. | |
| 5,676,666 A | 10/1997 | Oxland et al. | |
| 5,904,683 A | 5/1999 | Pohndorf et al. | |
| 6,106,526 A | 8/2000 | Harms et al. | |
| 6,120,503 A | 9/2000 | Michelson | |
| 6,224,602 B1 | 5/2001 | Hayes | |
| 6,231,610 B1 | 5/2001 | Geisler | |
| 6,342,055 B1 | 1/2002 | Eisermann et al. | |
| 6,436,142 B1 | 8/2002 | Paes et al. | |
| 6,454,771 B1 | 9/2002 | Michelson | |
| 6,695,845 B2 | 2/2004 | Dixon et al. | |
| 6,830,571 B2 | 12/2004 | Lenke et al. | |
| 7,909,860 B2 * | 3/2011 | Rathbun et al. | 606/290 |
| 2002/0045899 A1 | 4/2002 | Errico et al. | |
| 2002/0095155 A1 * | 7/2002 | Michelson | 606/61 |

(Continued)

OTHER PUBLICATIONS

EBI® VueLock® Anterior Cervical Plate System, Spine Universe, http://www.spineuniverse.com/displayarticle.php/article2992.html, (last visited Dec. 10, 2008).

(Continued)

Primary Examiner — Kevin T Truong
Assistant Examiner — Larry E Waggle, Jr.
(74) Attorney, Agent, or Firm — Ober, Kaler, Grimes & Shriver; Royal W. Craig; Christopher F. Lonegro

(57) ABSTRACT

A surgical staple for discectomy by an anterior approach that comprises a plate with sharp-pointed projections positioned at each of four corners of the plate and extending perpendicularly there from for frictional insertion into pilot holes formed in the vertebrae, and a pair of circular apertures in the plate spaced along a centerline for insertion of bone screws. The plurality of projections may further comprise four barbed and pointed projections that a surgeon may quickly tap into the bone, thereafter securing the staple with two smaller bone screws. An Annular C shaped retention locking clip retains the bone screws and prevents counter-rotation and back out.

11 Claims, 6 Drawing Sheets

U.S. PATENT DOCUMENTS

| | | | |
|---|---|---|---|
| 2002/0173790 A1 | 11/2002 | Chang et al. | |
| 2002/0183756 A1 | 12/2002 | Michelson | |
| 2003/0036759 A1 | 2/2003 | Musso | |
| 2003/0208204 A1 | 11/2003 | Bailey et al. | |
| 2004/0127900 A1* | 7/2004 | Konieczynski et al. | 606/69 |
| 2005/0021032 A1 | 1/2005 | Koo | |
| 2005/0059971 A1 | 3/2005 | Michelson | |
| 2005/0137597 A1 | 6/2005 | Butler et al. | |
| 2005/0149027 A1* | 7/2005 | Campbell et al. | 606/70 |
| 2005/0177161 A1 | 8/2005 | Baynham et al. | |
| 2005/0192576 A1 | 9/2005 | Michelson | |
| 2005/0192577 A1* | 9/2005 | Mosca et al. | 606/69 |
| 2006/0161157 A1* | 7/2006 | Mosca et al. | 606/69 |
| 2006/0241597 A1 | 10/2006 | Mitchell et al. | |

OTHER PUBLICATIONS

New Anterior Cervical Plate Makes Headlines, http://www.spineuniverse.com/displayarticle.php/article1535.html, (last visited Dec. 10, 2008).

Reflex Anterior Cervical Plate System, Stryker Corporation, http://www.stryker.com/en-us/products/Spine/Cervical/index.htm (last visited Dec. 10, 2008).

* cited by examiner

ANTERIOR CERVICAL STAPLE

CROSS-REFERENCE TO RELATED APPLICATIONS

The present application derives priority from provisional application 60/965,471 filed on Aug. 20, 2007.

BACKGROUND OF THE INVENTION

1. Field of the invention

The present invention relates to a surgical staple for discectomy by anterior approach to the cervical spine.

2. Description of the Background

Spinal stenosis is a medical condition in which the spinal canal narrows and compresses the spinal cord and nerves causing pain and neural degeneration. This is commonly due to spinal degeneration that naturally occurs with aging but can also be caused by spinal disc herniation (from trauma for example), osteoporosis, tumor or a variety of other causes. Stenosis may occur at any point along the spinal column but is more prevalent in the cervical and lumbar regions of the spine.

Cervical discectomy is a surgical procedure for treating spinal stenosis and disc herniation in the cervical region. Removal of the intervertebral disc and often the vertebral lamina (laminectomy) can relieve pressure from the spinal cord and neural structures. To maintain the stability of the spine in the absence of one or more intervertebral discs, spinal fusion is performed to immobilize the vertebrae.

Spinal fusion or spondylosyndesis is a surgical technique used to combine two or more vertebrae. Supplementary bone graft tissue is used in conjunction with the body's natural osteoblastic processes. A variety of approaches to fusion are available including posterolateral fusion which places the bone graft between the transverse processes in the back of the spine and anterior or posterior interbody fusion which places the bone graft between the vertebra in the area usually occupied by the intervertebral disc.

In most cases fusion is augmented by a process called fixation in which metallic screws, rods, plates or cages are implanted to stabilize the vertebra and facilitate bone fusion. The addition of hardware such as a cervical plate has been shown to maintain the stability of the graft/host junction increasing the chance of successful fusion. Conventional plates come in a basic construct of thin piece of metal and four screws that secure them to the bone. The typical screws are large and bulky. More recently narrow plates have emerged that use only two screws. There are benefits and drawback to both of these constructs.

Large plates and multiple screws offer a solid fixation but are bulky, use large screws, and require significant retraction for cases of multiple fixations which may lead into patients suffering from swallowing difficulties and possible changes in voice. Narrow plates with only two screws offer little fixation but minimize the hardware and intrusion. A variety of designs for spinal fixation devices have been proposed over the years although none have been entirely satisfactory.

It would be greatly advantageous to provide an anterior cervical staple for cervical fusion that: (1) allows for a more precise and a much smaller profile of fixation than prior art devices, (2) imposes less traction on the esophagus and trachea than prior art devices, (3) is lightweight, and (4) is inexpensive to manufacture and be applied for widespread use.

SUMMARY OF THE INVENTION

It is an object of the present invention to provide an anterior cervical staple that allows for a precise, small profile of fixation.

It is yet another object to provide an anterior cervical staple that imposes little traction on the esophagus and trachea.

It is yet another object to provide a cervical staple that is strong and rigid yet lower profile.

Still another object is to provide an anterior cervical staple that is lightweight.

In accordance with the foregoing objects, the present invention comprises a surgical staple for the anterior approach that includes a plate with sharp-pointed projections positioned at each of four corners of the plate and extending perpendicularly there from for frictional insertion into pilot holes formed in the vertebrae, and a pair of circular apertures in the plate spaced along a centerline for insertion of bone screws. The plurality of projections further comprise four barbed and pointed projections that a surgeon may quickly tap into the bone, thereafter securing the staple with two smaller bone screws. This leads into a quicker implant application, less retraction as it may be done individually for each level and much stronger fixation than two screws alone.

BRIEF DESCRIPTION OF THE DRAWINGS

Other objects, features, and advantages of the present invention will become more apparent from the following detailed description of the preferred embodiment and certain modifications thereof, in which.

DETAILED DESCRIPTION OF THE PREFERRED EMBODIMENTS

Figure 1:
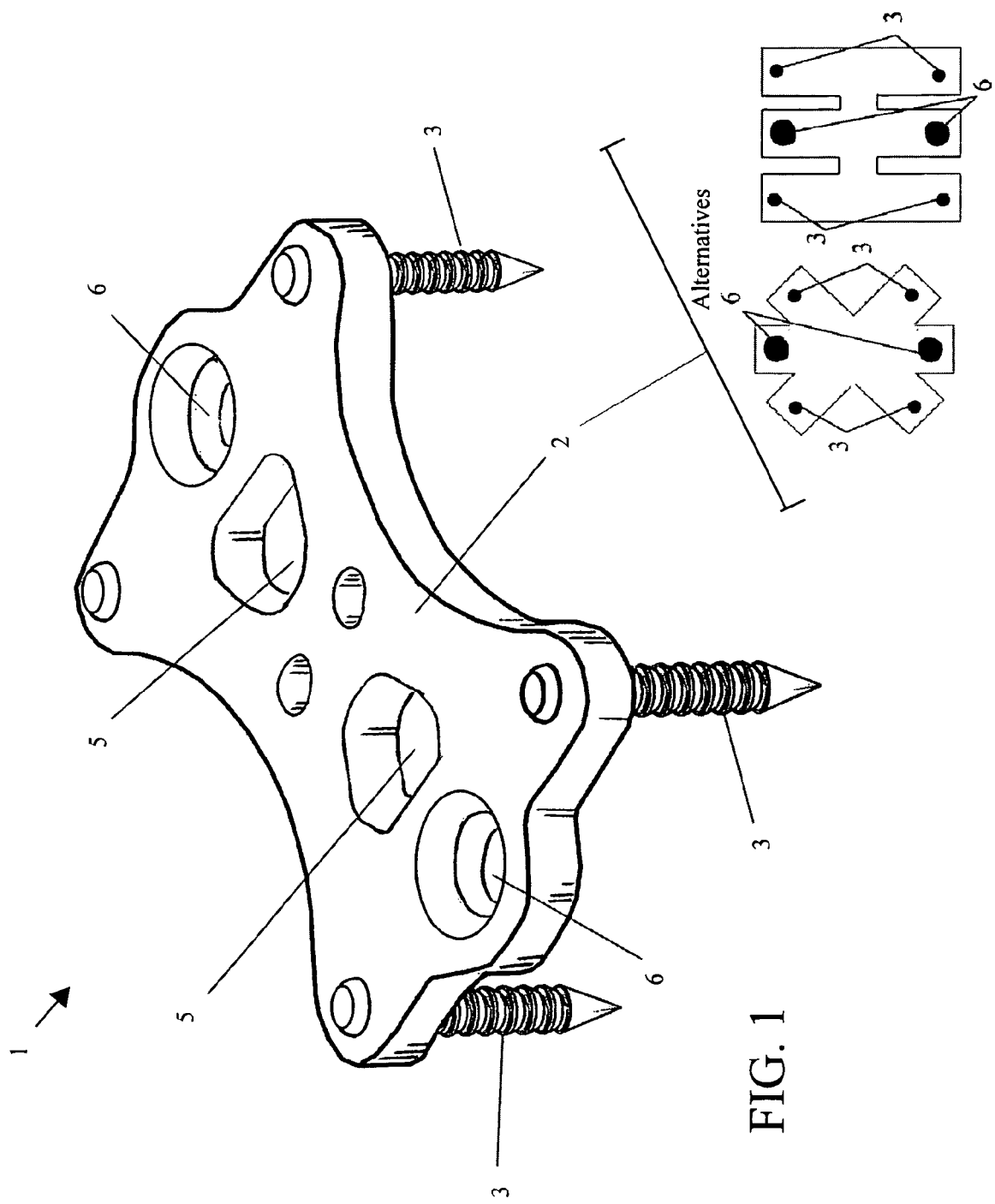
FIG. 1 is a front perspective view of an embodiment of the staple.
Figure 2:
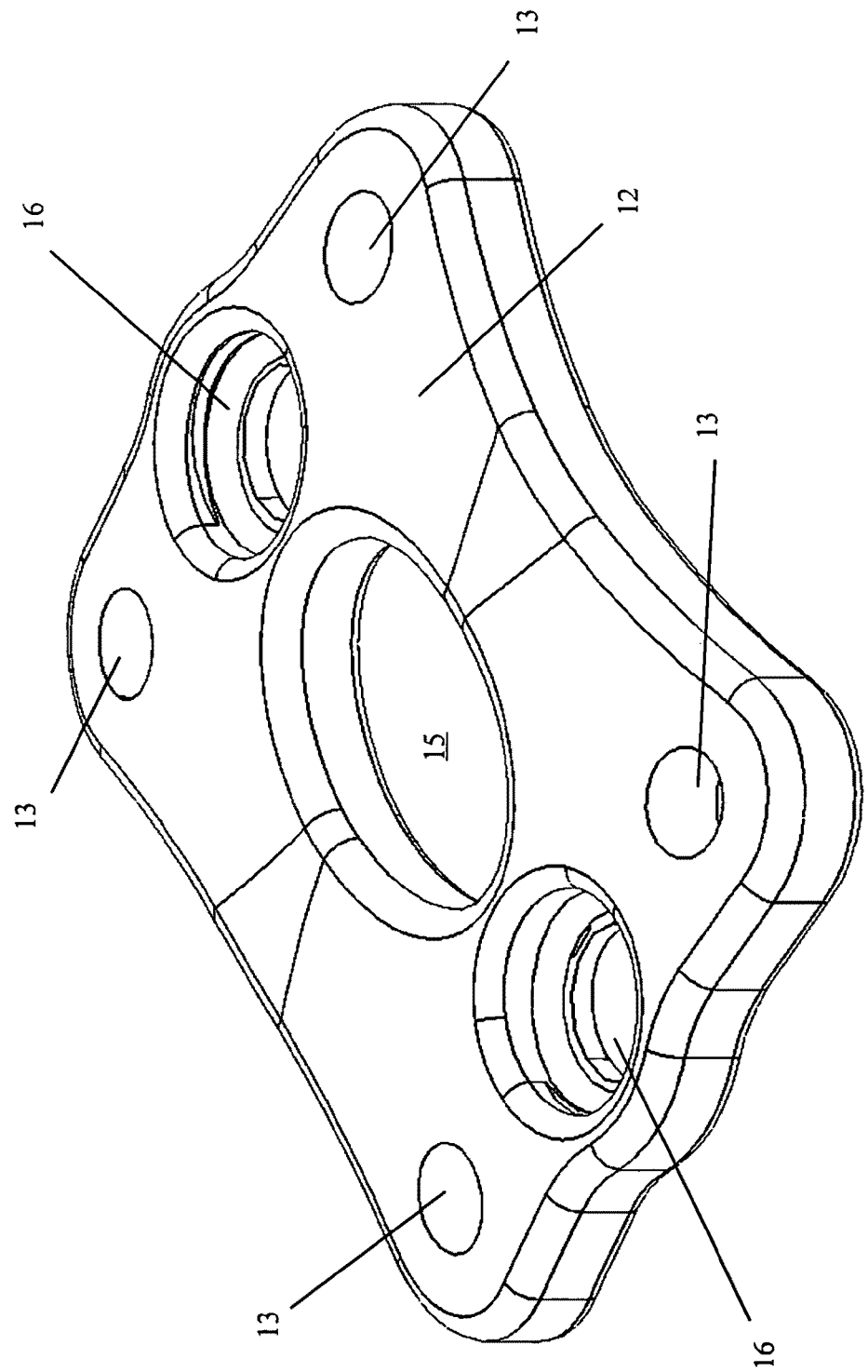
FIG. 2 is a front perspective view of another embodiment of the staple without the pins welded in place.

The present invention comprises a staple for anterior fusion. FIG. 1 is a front/oblique perspective view of an embodiment of the staple 1. The staple 1 as depicted in FIG. 1 includes a substantially planar plate 2 with a plurality of projections 3. The projections 3 are positioned at each of the four corners of the plate 2 and extend downwardly in a perpendicular direction from the bottom surface of the plate 2. The projections 3 may be separate components press-fit through holes in the plate 2 or may be integrally formed therewith. The projections 3 are preferably barbed (such as, for example, with concentric annular teeth as shown in FIG. 1) and terminate in a pointed distal end to facilitate their insertion into the vertebrae. The plurality of projections 3 provide for the staple 1 to be quickly hammered into the vertebrae V after a discectomy is done and bone graft is in place, as opposed to fixating the plate with four screws in a conventional manner.

The body of the plate 2 includes two central inline gumdrop openings 5 proximate to and directed inward toward each other. The gumdrop openings 5 allow visualization of the graft through radiography. The plate 2 also includes a circular aperture 6 at each of the distal corners of the plate 2. The circular apertures 6 allow screws to penetrate through the plate and into the bone. Each circular aperture 6 is centrally located between the respective projections 3 at each end of the plate 2, outside the gumdrop openings 5 and in alignment therewith.

The exact shape of the anterior staple 1 and plate 2 are a matter of design choice. The essential utility lies in the fact that it is equipped with four corner projections 3 and two inline circular apertures 6 for screws. Other staples 1 with these features have the requisite components. For example, the projections 3 and circular apertures 6 may be connected together by any other suitable plate 2, such as a star-shaped plate 2 or double-H shaped plate as seen in the inset of FIG. 1.

Figure 3A:
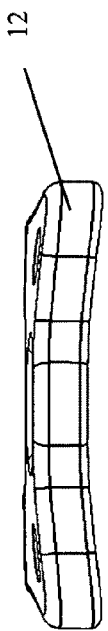
FIG. 3a is a top view of an embodiment of the staple without the pins welded in place.
Figure 3B:
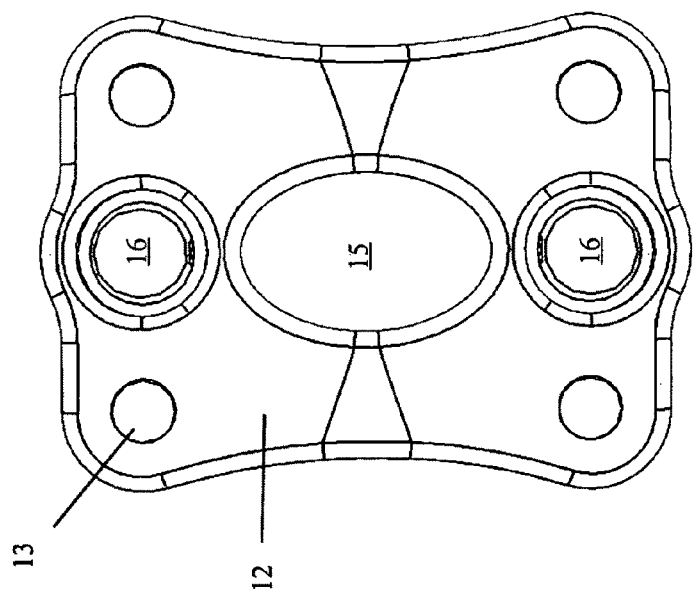
FIG. 3b is a side view of an embodiment of the staple.
Figure 3C:
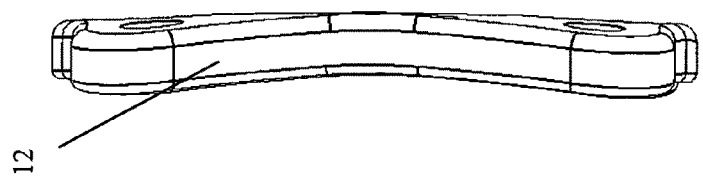
FIG. 3c is an end view of an embodiment of the staple.
Figure 3D:
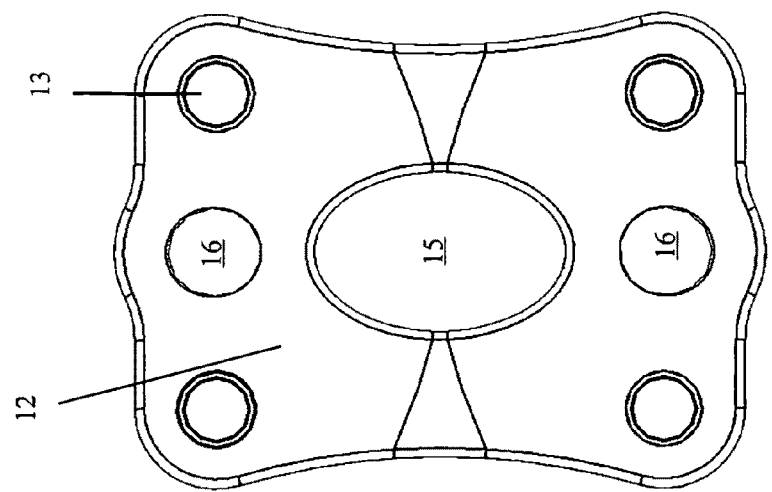
FIG. 3d is a bottom view of an embodiment of the staple.

FIGS. 2 and 3a through 3d depict yet another embodiment of the plate 12. In this alternate embodiment of the plate, circular screw apertures 16 remain at opposite ends of the plate along its midline and between the pair of projections 3 (not shown) at each end of the plate. Four apertures 13 are depicted for receiving projections 3 in this embodiment. As previously observed, projections 3 may also be integrally formed with plate 12. Gumdrop openings 5 have been enlarged and merged to form a single ovoid opening 15. As best seen in FIGS. 3b and 3c, the plate 12 is formed with a gentle concave curvature on both of the major planar axes. This compound curvature provides better cooperation between the plate 12 and the vertebra. The sides of the plate 2, 12 are tapered inward as seen in FIGS. 1 and 3a, 3d and have a smooth contoured surface to prevent perforations of the vessels proximate the vertebral column.

All of the above components can be constructed of durable, surgically, implantable material such as titanium or stainless steel. The staple 1 possesses a simple and scalable design and may be fabricated of other lightweight materials providing an appropriate degree of flexibility, resiliency, durability, and longevity. Also, the staple 1 is inexpensive to manufacture and sell, to provide for widespread use.

Figure 4:
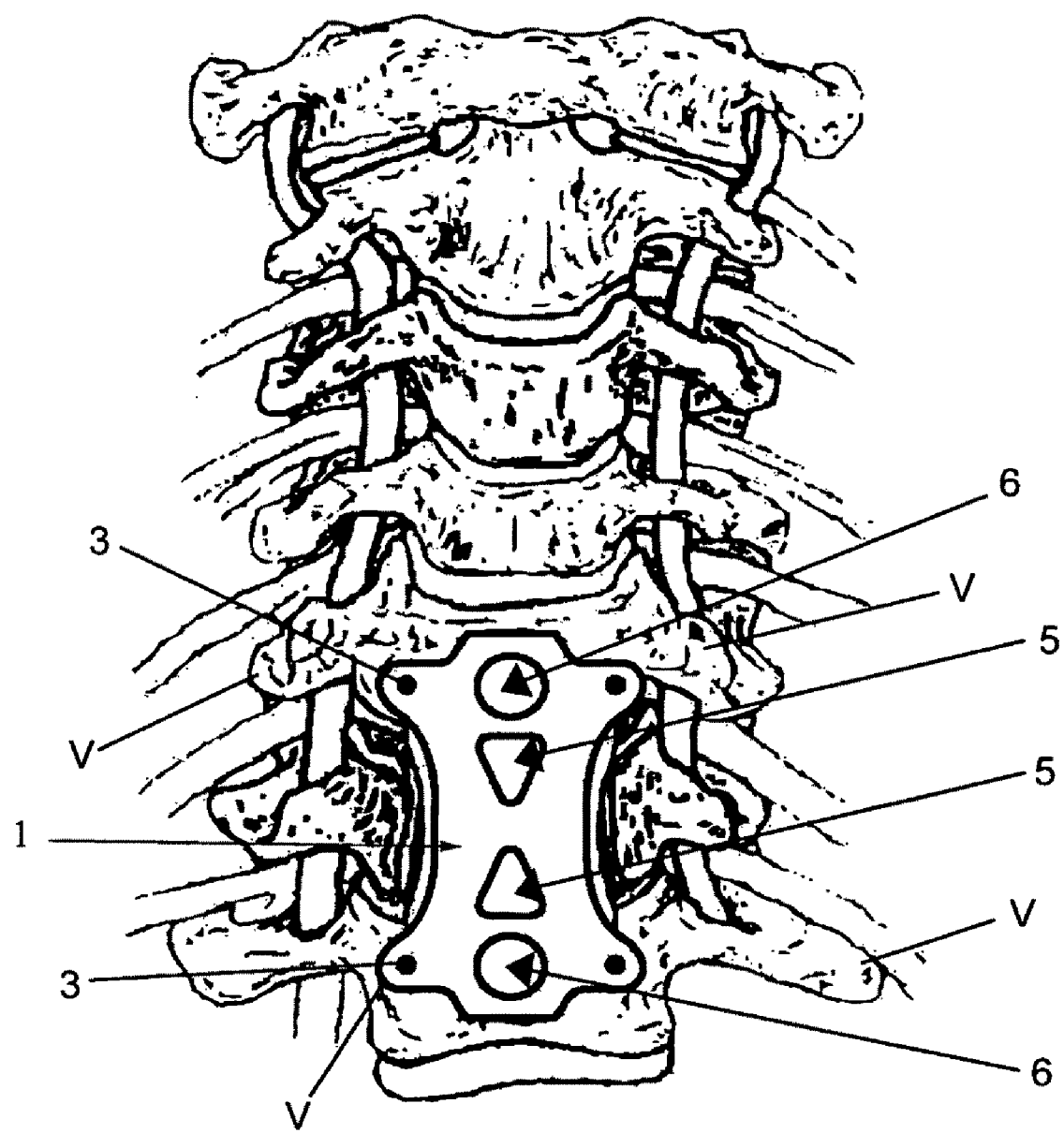
FIG. 4 shows an embodiment of the staple affixed to the vertebrae.

FIG. 4 shows the staple 1 affixed to the vertebrae V. The staple 1 is of sufficient length to span the disc space between two adjacent vertebrae V. The staple 1 engages, via projections 3, the vertebrae V adjacent to that disc space.

The staple 1 according to the present invention is broadly applicable to the anterior, posterior and lateral aspects of the spinal column, including the cervical, thoracic or lumbar area. The staple 1 is especially beneficial in performing cervical facet fusion by the anterior approach (from the front of the neck), which can provide exposure from C2 down to the cervico-thoracic junction. Under this approach, only one thin vestigial muscle needs to be cut (after a skin incision is made), after which anatomic planes can be followed right down to the seven vertebra V of the cervical spine. Next, the surgeon retracts tissues and muscles and identifies the disc space that is in need of repair. Complete discectomy is performed and a bone graft is applied to the defect.

A suitable drilling instrument such as a Universal Bone Drill—S. S. Gears (Cat. No. 320-010), Micro Hand Drill (Cat. No. 320-020), Universal Open Hand Drill—S. S. Gear (Cat. No. 320-030) is then used to create insertion holes in the vertebrae above and below the removed disk for receiving the projections 3 of the staple 1. The staple 1 is applied across the disc space aligning projections 3 with the insertion holes as seen in FIG. 4. The surgeon drives the staple 1 into the bone V by applying a high impact force via a driving instrument such as a surgical mallet. The staple 1 is driven into the bone V until the projections 3 are fully inserted into the insertion holes, and the bottom surface of the top plate 2 rests against the surface of the vertebrae V. Next, conventional bone screws are inserted into the circular apertures 6 in the top plate 2 and into the vertebrae V for the purpose of stabilization.

Figure 5:
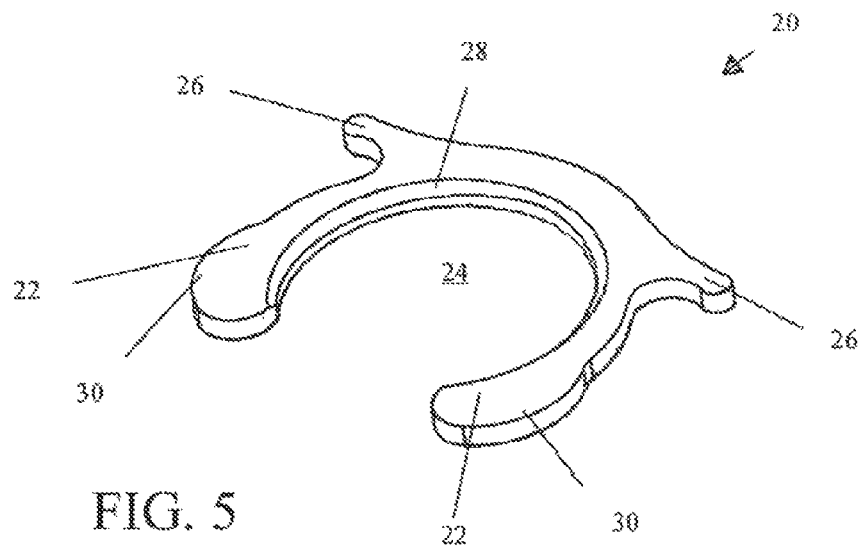
FIG. 5 is a perspective view of an embodiment of the screw locking clip.
Figure 6:
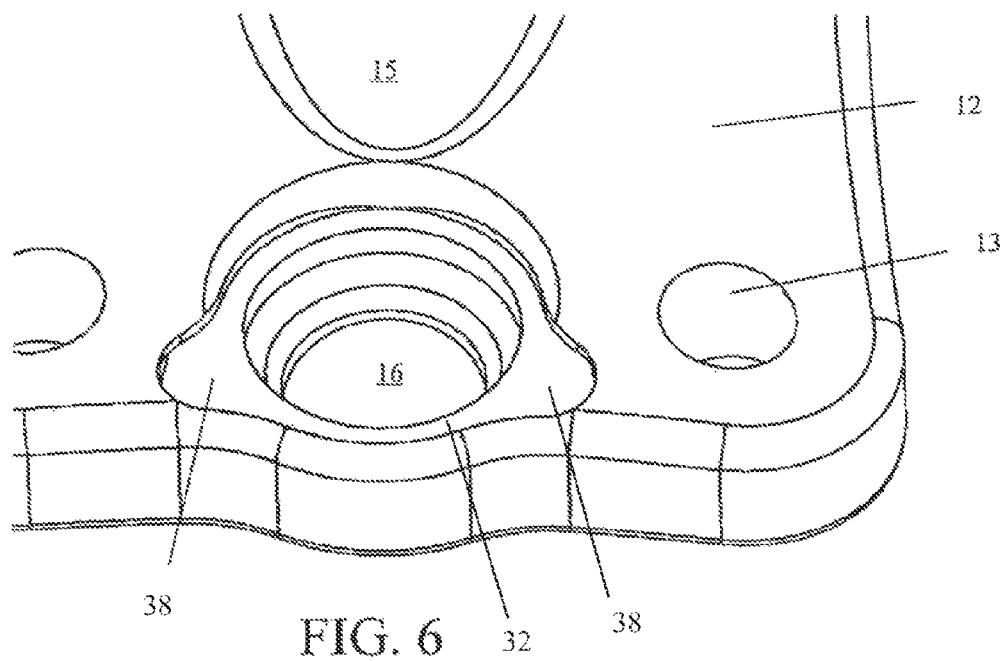
FIG. 6 is a perspective view of an embodiment of the locking clip recess in the plate.
Figure 7:
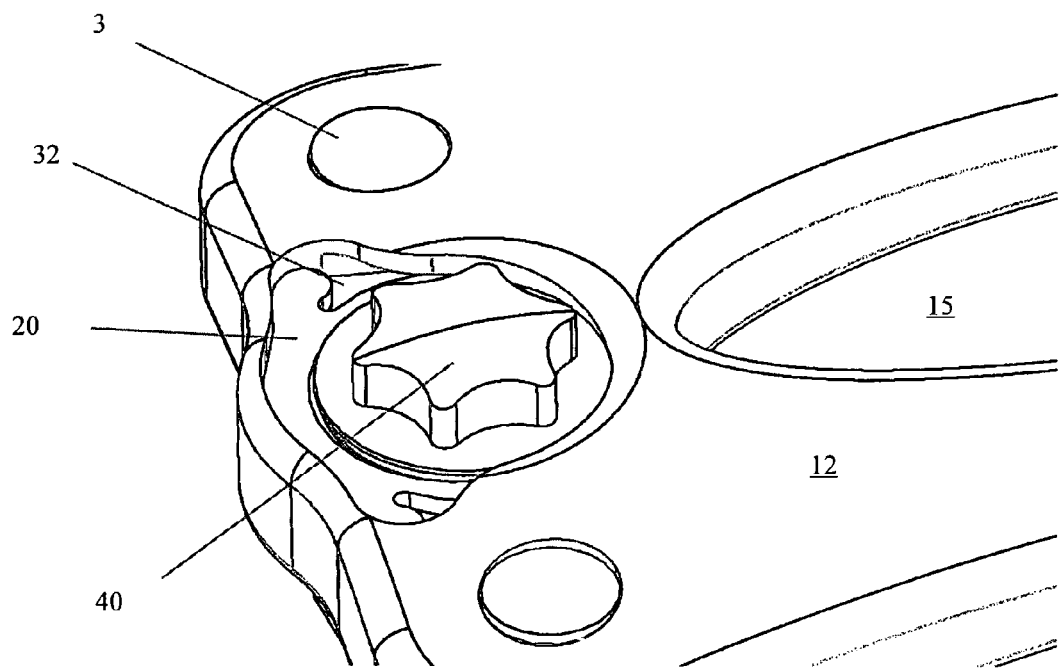
FIG. 7 is a perspective view of an embodiment of the screw locking mechanism of the staple

FIGS. 5-7 illustrate an optional locking clip 20 that may be utilized in cooperation with plates 2, 12 or other embodiments of the invention to prevent counter-rotation and loosening of the bone screws inserted into apertures 6. With reference to FIG. 5, locking clip 20 is primarily "C" or "U" shaped having two arms 22 tracing an incomplete arc around a central aperture 24. As seen in FIG. 6, the locking clip 20 seats within a conforming recess 32 formed about the apertures 6 and grips the bone screws inserted into the apertures 6. With combined reference to FIGS. 5-6, a pair of extensions 26 are keyed to the lobes 38 of the recess 32 of plates 2, 12 to prevent counter rotation of the bone screws. Extensions 26 are provided at the exterior of the arc opposite the opening in the arc as seen in FIG. 5. It should be understood that the location of the extensions in relation to the opening of the "C" may be other than as depicted. A single extension may also be utilized, preferably but not necessarily directly opposite the opening of the "C". The top interior surface of the arms 22 are provided with a bevel 28 to form a frustum encircling aperture 24. The distal ends of arms 22 may be provided with a widened profile at flares 30.

Locking clip 20 operates in cooperation with recess 32 in the surface of plates 2, 12 around aperture 6, 16, as depicted in FIG. 6. Recess 32 is shaped to receive locking clip 22 in the recess such that the aperture 24 is generally aligned with the circular aperture 6, 16 of the plate 2, 12. On insertion the extensions 26 abut the outer wall 34 of the recess preventing lateral movement in that direction. The extensions 26 may be affixed to the plate 2, 12 via small welds (as depicted), by micro-screws, or by seating them inside a pocket or overhanging lip formed on the plate 2, 12. The diameter of aperture 24 of the "C" is slightly smaller than the diameter of circular aperture 6, 16 such that the arms 22 project over aperture 6, 16 when the locking clip 20 is inserted into the recess 32. An annular groove 36 is provided in the interior surface of the circular aperture 6, 16 for receiving and retaining arms 22.

Figure 8:
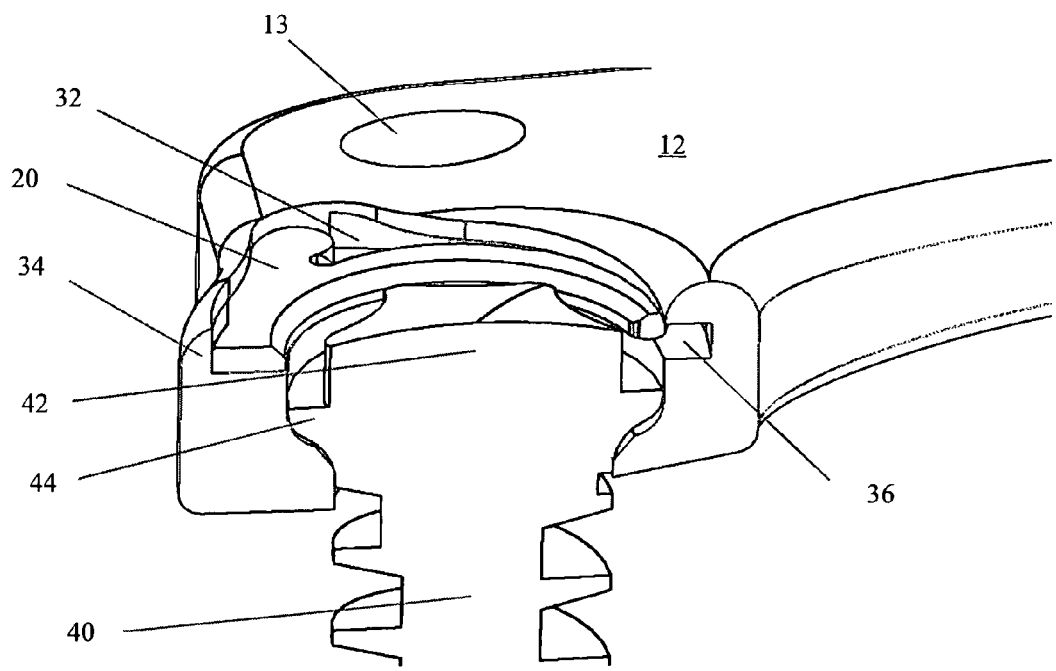
FIG. 8 is a section view of an embodiment of the screw locking mechanism of the staple

As seen in FIGS. 7 and 8 a bone screw 40 having a head 42 and a lip 44 is inserted into the aperture 6, 16 and driven into the bone. The lip 44 is formed with an upward flare or taper, which may be frusto-conical or fluted. Upon insertion, as the tapered lip 44 encounters the bevel 28 of the locking clip 20 it forces the arms 22 of the "C" to spring open into the annular groove 36 allowing the head 42 and lip 44 of the screw 40 to pass. Once the screw 40 has passed the arms 22 spring back to their original shape projecting over the aperture 6, 16. Engagement of the widened arms 22 in the groove 36 resist any counter-rotation or reversing action of the screw 40. Because the underside of the clip 20 is not beveled the arms 22 will not spring open to permit the screw to back out.

Locking clip 20 may can be constructed of durable, surgically implantable metal such as titanium or stainless steel or other lightweight materials providing an appropriate degree of flexibility, resiliency, durability, and longevity such as Polyetheretherketone (PEEK).

It should now be apparent that the above-described anterior cervical staple provides for strong and robust fixation despite a precise, small profile, and yet it is lightweight and it imposes very little traction on the esophagus and trachea.

Having now fully set forth the preferred embodiments and certain modifications of the concept underlying the present invention, various other embodiments as well as certain variations and modifications of the embodiments herein shown and described will obviously occur to those skilled in the art upon becoming familiar with said underlying concept. It is to be understood, therefore, that the invention may be practiced otherwise than as specifically set forth in the appended claims.

I claim:

1. A surgical staple for fixation of the spinal vertebrae, comprising:
    a plate having a top side and a bottom side, said top side characterized by a pair of non-round recessed areas spaced along a centerline of the plate, said recessed areas joined to said top surface by a side wall and characterized by a generally circular portion conjoined with a first lobe and a second lobe extending there from positioned symmetrically on either side of an axis through a center of a circular aperture within each said generally circular portion of said recessed areas, said side wall further comprising a partial or complete annular groove around said generally circular portion;
    a plurality of sharp-pointed projections positioned at the periphery of the plate extending perpendicularly from the bottom side for frictional insertion into pilot holes formed in the vertebrae;
    said circular aperture within each said generally circular portion of said recessed areas for insertion of a bone screw, said circular apertures defined by a first diameter at said recessed area and a second, smaller diameter at said bottom side; and
    a "C" or "U" shaped locking clip comprising a first arm and a second arm incompletely encircling a central opening and a third arm and a fourth arm extending from between said first and second arms of said locking clip, said third arm and said fourth arm symmetrically opposed to each other about an axis through a center of said central opening of said "C" or "U" shape and an opening between said first and second arms, said central opening having a third diameter less than said first diameter, said locking clip retained in each said recessed area such that said third arm abuts said side wall within said first lobe and said fourth arm abuts said side wall within said second lobe and a distal portion of said arms are received within said annular groove when said central opening is substantially aligned with said circular aperture and wherein an outer edge of both said third arm and said fourth arm are continuously arcuate, said recessed area having a cooperative arcuate segment between said lobes such that a force applied along said axis through the center of said "C" or "U" shape and said opening between said first and second arms seats said clip against said segment and prevents later motion thereof,
    whereby insertion of said bone screws will cause said first and second arms to spring open and allow said bone screw to pass and then close to their original shape to prevent said screw from withdrawing.

2. The surgical staple of claim 1 further comprising a plurality of apertures within the plate between said recessed areas for non-invasive inspection of the vertebrae.

3. The surgical staple of claim 1 wherein the said plate is concave about at least one major axis with respect to the bottom side.

4. The surgical staple of claim 1 wherein said sharp pointed projections are barbed along their exterior surface.

5. The surgical staple of claim 1 wherein an upper interior surface of said first and second arms of said locking clip is beveled.

6. A bone screw locking mechanism adapted to inhibit withdrawal of a bone screw installed in an aperture of a spinal fixation plate, the bone screw locking mechanism comprising:
    a recessed area joined to a surface of said plate by a side wall and characterized by a generally circular portion conjoined with a first lobe and a second lobe extending there from, said first and second lobes positioned symmetrically on either side of an axis through a center of said aperture, said side wall further comprising an annular groove extending at least partially around said generally circular portion; and
    a generally "C" or "U" shaped locking clip having a first arm and a second arm incompletely encircling a central opening and a third arm and a fourth arm extending from between said first and second arms of said locking clip, said third arm and said fourth arm symmetrically opposed to each other about an axis through a center of said central opening of said "C" or "U" shape and an opening between said first and second arms, said locking clip retained in said recessed area such that said third arm abuts said side wall within said first lobe and said fourth arm abuts said side wall within said second lobe and a distal portion of said arms are received within said annular groove when said central opening is substantially aligned with said aperture and wherein an outer edge of said third arm and said fourth arm is continuously arcuate, said recessed area having a cooperative arcuate segment between said lobes such that a force applied along said axis through the center of said "C" or "U" shape and said opening between said first and second arms seats said clip against said segment and prevents later motion thereof,
    the central opening of said locking clip being substantially aligned with said aperture of said plate and being smaller than said aperture of said plate in at least one direction such that insertion of said bone screw will cause said first and second arms to spring open and allow said bone screw to pass and then close to their original shape to prevent said screw from withdrawing.

7. The bone screw locking mechanism of claim 6 wherein an upper interior surface of said first and second arms of said locking clip is beveled.

8. The bone screw locking mechanism of claim 6 wherein said locking clip is welded to said plate.

9. The bone screw locking mechanism of claim 6 wherein said locking clip is riveted to said plate.

10. The bone screw locking mechanism of claim 6 wherein said locking clip is affixed to said plate by micro-screws.

11. The bone screw locking mechanism of claim 6 wherein said locking clip affixed to said plate by insertion into said groove.

* * * * *